United States Patent [19]
Bolton

[11] Patent Number: 5,514,144
[45] Date of Patent: May 7, 1996

[54] DRILL GUIDE DEVICE FOR THE ARTHROSCOPIC ANATOMIC PLACEMENT OF A STRAIGHT TIBIO-FEMORAL BONE TUNNEL FOR ACL RECONSTRUCTION

[76] Inventor: Carl W. Bolton, 2110 de la Vina #2, Santa Barbara, Calif. 93105

[21] Appl. No.: 173,675

[22] Filed: Dec. 20, 1993

[51] Int. Cl.⁶ .................................................. A61B 17/56
[52] U.S. Cl. .................................................. 606/96
[58] Field of Search ................................. 606/96, 98, 99

[56] References Cited

U.S. PATENT DOCUMENTS

| | | |
|---|---|---|
| 4,257,411 | 3/1981 | Cho . |
| 4,535,768 | 8/1985 | Hourahane et al. . |
| 4,672,957 | 6/1987 | Hourahane . |
| 4,708,139 | 11/1987 | Dunbar, IV . |
| 4,739,751 | 4/1988 | Sapega et al. . |
| 4,772,286 | 9/1988 | Goble et al. . |
| 4,781,182 | 11/1988 | Purnell et al. . |
| 4,901,711 | 2/1990 | Goble ........................................ 606/96 |
| 4,920,958 | 5/1990 | Walt et al. ................................. 606/96 |
| 4,945,904 | 8/1990 | Bolton et al. ............................. 606/96 |
| 5,112,335 | 5/1992 | Laboureau et al. ....................... 606/96 |
| 5,152,764 | 10/1992 | Goble ....................................... 606/96 |
| 5,234,434 | 8/1993 | Goble et al. .............................. 606/96 |
| 5,242,444 | 9/1993 | MacMillan ................................ 606/96 |

OTHER PUBLICATIONS

Stryker–Isometric Drill Guide. Jan. 1985. Product #170–55.
Richard Wolf Medical–Hendler Uni–tunnel Drill Guide System.

*Primary Examiner*—Tamara L. Graysay

[57] ABSTRACT

The invention provides a drill guide device to accurately place a straight bone tunnel through the tibia and into the femur, the axis of which passes through the anatomic points of origin and insertion of the anterior cruciate ligament. A unique feature of the invention is that by virtue of the linkage mechanism for variable length adjustment, it can simultaneously select on two reference points within a joint thereby allowing for the sequential drilling of the bone tunnels in a straight line incorporating both of the reference points. The method of use for this drill guide device is intended to be positioned through an arthroscopic portal and does not require a femoral incision.

12 Claims, 11 Drawing Sheets

DRILL GUIDE DEVICE FOR THE ARTHROSCOPIC ANATOMIC PLACEMENT OF A STRAIGHT TIBIO-FEMORAL BONE TUNNEL FOR ACL RECONSTRUCTION

FIELD OF THE INVENTION

A drill guide designed to accurately place a straight bone tunnel through the tibia and into the femur, the axis of which passes through the anatomic points of origin and insertion of the anterior cruciate ligament [ACL], when the knee is in approximately ninety degrees of flexion. The method of use for this drill guide is intended to be positioned through an arthroscopic portal and does not require a femoral incision.

BACKGROUND OF THE INVENTION

There have been extensive advancements over the past fifteen years in terms of surgical reconstruction of the anterior cruciate ligament deficient knee. Not only have the technics for repair and/or reconstruction evolved but so have the selection of materials utilized in these surgical procedures. There are a variety of materials, such as heterografts, allografts, autografts and synthetics, that have been used. This natural evolutionary process is by no means final, however it has become clear that there is an obvious prediliction for the use of biological tissue when it comes to making the selection for the most appropriate material for ACL reconstruction. In concert with this evolutionary process has been a greater awareness and understanding in regards to the natural history of this particular injury pattern as well as a more aggressive approach to post surgical rehabilitation. Of tantamount inportance during this learning period has been an acute appreciation in the necessity for surgical precision and reduced patient morbidity.

Without adequate emphasis directed toward precise surgical detail, even the most appropriately selected material will be fraught with a host of potential problems including; flexion contractures, patello-femoral pain, loss of range of motion, and frank failure of the reconstruction with resultant instability. The secondary restraints of the knee, as well as the menisci, are further jeopardized with the return to the previous level of instability. It goes without saying that technical surgical precision is fundamentally important for the successful outcome of the surgical procedure. This in fact is borne out by the dramatic growth in the surgical instrumentation market, as well as the advancements developed with arthroscopic techniques. One feature which has enhanced the accuracy of the surgical procedure has been the utilization of drill guides to aid in the precision of bone tunnel placement in the proximal tibia and distal femur. There are no less than two dozen drill guides that have been developed over the past two decades which are intended to provide increased accuracy of bone tunnel placement; some to a lesser or greater degree.

It is not the intent of this application to address all of the different drill guide concepts that have been reviewed for the purpose of this application but to address only those which embody similar ideas as embodied in the scope of this application. As with most drill guides utilized in cruciate ligament reconstructive procedures, the primary intent is to place a through-and-through tunnel in the proximal tibia originating externally on the tibial cortex just medial to the tibial tuberosity and exiting at the pre-selected anatomic insertion site of the ACL on the tibial plateau. Some guides have an additional modification of the tibial component which is then utilized to create the femoral tunnel. There are many variations of the method to create the femoral tunnel which include; anatomic versus over-the-top, through-and-through tunnel versus blind femoral tunnel, accessing the tunnel externally and exiting intra-articularly versus accessing the tunnel intra-articularly on the anatomic origin of the ACL. Most often the axes of the femoral and tibial tunnels are placed independent of one another. Those drill guides which index from the axis of one tunnel to create the axis of the second tunnel will be discussed here as that is one of the critical factors within the scope of this application.

Currently there are five drill guide concepts which embody the concept of attempting to achieve alignment of the tibial and femoral bone tunnels such that they follow a single axis or at least attempt to achieve alignment in a single plane. For example, secondary placement of the femoral tunnel can be indexed from the preplaced tibial tunnel such that the axes of both tunnels lies in a straight line (at a given knee flexion usually around ninety degrees) or that the axes of the two tunnels lie in the same plane relative to the flexion and extension of the knee. Those five drill guides which share these concepts include the following patents or product literature: Goble [U.S. Pat. No. 4,772,286 & 4,901,711], Laboureau [U.S. Pat. No. 5,112,335], Bolton [U.S. Pat. No. 4,945,904], Hendler Uni-Tunnel Drill Guide System [Manufacturerd by Richard Wolf Medical Instruments] and Isometric Drill Guide [Manufactured by Stryker]. Patents by Goble discuss details for placement of bony tunnels through the tibia and femur. In particular, U.S. Pat. No. 4,901,711 illustrates a drill guide that mounts to a preplaced K-wire fitted through a straight bone tunnel incorporating the attachment sites of the ACL. During the description for placement of the K-wire he describes the need of the surgeon to observe the placement by means of fluoroscopic and arthroscopic monitoring while the knee is maintained in approximately ninety degrees of flexion. While this technique provides for a straight tibio-femoral bone tunnel it is difficult at best to be certain that the bone tunnel will pass through the exact attachment sites of the ACL. Although Goble describes in his patent that while under fluoroscopic and arthroscopic control the guidewire can be driven through the tibia and across the cruciate ligament junctions with the proximal tibia and distal femur ends and into the femoral cortex, one can not be certain to accurately intersect the anatomic sites with the guidewire by starting the drilling at the external tibial cortex. Only through trial and error and repeated passes of the guidewire can one hope to properly position the guidewire such that it will create a straight path from the external tibial cortex through the tibial metaphysis entering the joint space at the anatomic insertion site of the ACL and then penetrating the femur at precisely the anatomic origin of the ACL. This of course can only be achieved with the knee maintained at approximately ninety degrees of flexion. In addition this method requires the use of fluoroscopy with its attendant expense, space-occupying problems in the operating room, radiation exposure hazards and along with the requisite skill necessary to use the equipment properly and to accurately interpret the image.

Other drill guide systems such as the Hendler Uni-Tunnel Drill Guide and the Isometric Drill Guide make mention of trying to achieve a straight tibio-femoral bone tunnel which passes through the anatomic origin and insertion sites of the ACL. The Hendler Uni-Tunnel system illustrates a drill guide system which allows for placement of a straight tibio-femoral bone tunnel alignment, however the intra-articular aiming device, while it can help to stabilize the guide pin as it passes through the joint space, can not accurately direct the guide pin to intersect precisely the anatomic sites of origin and insertion of the ACL. The intra-articular aiming device may be able to direct the guide pin to intersect either the femoral or tibial insertion site of the ACL but it is not able to simultaneously direct the guide pin to intersect both of the anatomic sites. Although this system can be utilized in conjunction with arthroscopic monitoring, it does require a femoral cut down procedure in order to position the femoral post against the lateral femoral cortex. Similar to the Hendler Uni-Tunnel system, the Isometric Drill Guide is intended to provide a straight tibiofemoral bone tunnel also while the knee is held in approximately ninety degrees of flexion. The Isometric Drill Guide requires an arthrotomy incision in order to introduce the relatively large aiming portion into the knee joint. The design of this drill guide system is such that the intra-articular portion of the guide is used to identify the attachment site on the tibial plateau, however it can not accurately identify the attachment site on the femur. Therefore, it is only by trial and error that placement of the guide pin will intersect the femoral anatomic site of the ACL. It also requires direct observation through the arthrotomy incision or by the aid of radiography in order to facilitate placement of the guide pin.

While Laboureau and Bolton describe drill guide systems that provide for placement of the tibial and femoral bone tunnels to be in the same plane; they do not allow for placement along a single straight axis. Laboureau goes on to claim that with his technique he can obtain an alignment of marking and drilling directions of the femur and tibial insertion tunnels when the knee is in extension. However, given the geometry of the knee joint it is not possible to obtain a straight tibio-femoral tunnel intersecting the anatomic sites of the ACL when the knee is in or near full extension. He further goes on to claim that with the knee in the extension position the prolongation of the femoral insertion tunnel is almost in the axis of the tibial insertion tunnel. Similar to the patent by Bolton, both of these drill guide designs result in the placement of the tibial and femoral bone tunnels in the same plane but certainly not along a single axis. Although in the patent described by Bolton the technique does allow for the axis of the tibial tunnel and the intraarticular segment to be in a straight line near full extension of the knee. However, the axis of the femoral tunnel relative to the axis of the tibial tunnel can only achieve the relationship of being in the same plane. Also, the drill guide systems of Laboureau and Bolton require a femoral cut down procedure and a through-and-through femoral bone tunnel, in addition the technique as described by Laboureau requires the use of teleradiography in order to properly locate the anatomic site of origin of the ACL.

The previously mentioned drill guide systems are intended to achieve a tibio-femoral bone tunnel relationship in which the alignment of the central axes of the two independent tunnels is in a straight line or in the same plane in regards to flexion and extension of the knee. While this may be the intention of the formerly described systems it is also apparent that they are not capable of providing an accurate, repeatedly reproducible, straight tibio-femoral bone tunnel which intersects the anatomic origin and insertion of the ACL. The achievement of this often sought after straight tibio-femoral bone tunnel configuration can be obtained, however generally only after trial and error with repeated passes of the guide pin. The only means by which to accurately and repeatably place the guide pin in a straight line intersecting the anatomic sites of the ACL is by means of a specially designed drill guide as described in this application. The direction today in terms of innovative development in surgical instrumentation is focused on several goals; precision, accuracy and repeatability, user friendly, simple and easy to use, reduction of patient morbidity, saves time, facilitation of the procedure for the surgeon, cost effective, minimally invasive, and nondisposable.

SUMMARY OF THE INVENTION

There are several features of the present invention that demonstrate clear advantages over formerly described drill guide systems. It is the object of this invention to provide a method for a drill guide device that will direct an accurate placement of a through-and-through bone tunnel in the proximal tibia and a bone tunnel in the distal femur (either a through-and-through tunnel or a blind tunnel) such that the central axes of the two tunnels lie in a straight line (while the knee is maintained in approximately ninety degrees of flexion).

It is also critical to the object of the present invention that the straight bone tunnel intersect the precise anatomic attachment sites for the ACL on the tibia and femur. A unique feature of this design is that it is possible to directly visualize, via arthroscopy, the primary and secondary reference pointers simultaneously positioned on the precise anatomic sites of origin and insertion of the ACL and to maintain that position while drilling with the guide pin.

It is also critical to the object of the present invention that while the device will allow for a straight tibio-femoral bone tunnel, as the knee is in approximately ninety degrees of flexion, the axes of the tibial through-and-through bone tunnel and of the intra-articular segment will remain in a near straight line throughout the full range of motion, thereby minimizing adverse stress concentrations imposed on the ACL replacement material as it passes over the exit site of the tibial tunnel.

It is also the object of the present invention that it be used in conjunction with arthroscopic means such that the configuration of the primary and secondary reference pointers is capable of being introduced into the knee joint through one of the arthroscopic portals, most preferrably the anteromedial postal.

Another object of the present invention is that the drill guide is self-retaining, such that after the anatomic attachment sites of the ACL have been selected by the respective reference pointers, the guide sleeve with conjoined guide sleeve arm is engaged with the guide sleeve alignment arm and advanced until it comes in contact with external tibial cortex and is secured in this position, thereby rendering the system self retaining.

Another unique feature of the present invention is in the configuration of the linkage mechanism for variable length adjustment which accomodates for the variation in length of the ACL in different size patients. This feature further adds to the inherent precision required for this type of surgical procedure, such that the drill guide device described herein can be adjusted for any size of patient.

Still another object of the present invention is that the use of this drill guide device does not require a femoral cut down procedure. Other drill guide systems often require a femoral cut down to expose a portion of the femoral cortex or to gain access to the ACL attachment site via the posterior capsule. The preparation for both tunnels with the drill guide of the present invention is performed through a single tibial incision and via the arthroscopic portal.

Still another object of the present invention is that it allows for a more accurate measurement of isometricity by virtue of the fact that the small diameter of the initial tunnels made with the guide pins provides a far more accurate representation of the true central path for the replacement graft than that of the subsequent larger diameter bone tunnels. Therefore the isometric measurement is best determined by placing a trial suture through the tunnel created by the guide pin and connecting it to an isometer in order to more precisely reflect the actual isometric placement of the tunnel position.

It is also inherent in the design of the present invention that it is simple and easy to use.

DETAILED DESCRIPTION OF THE INVENTION

Figure 1:
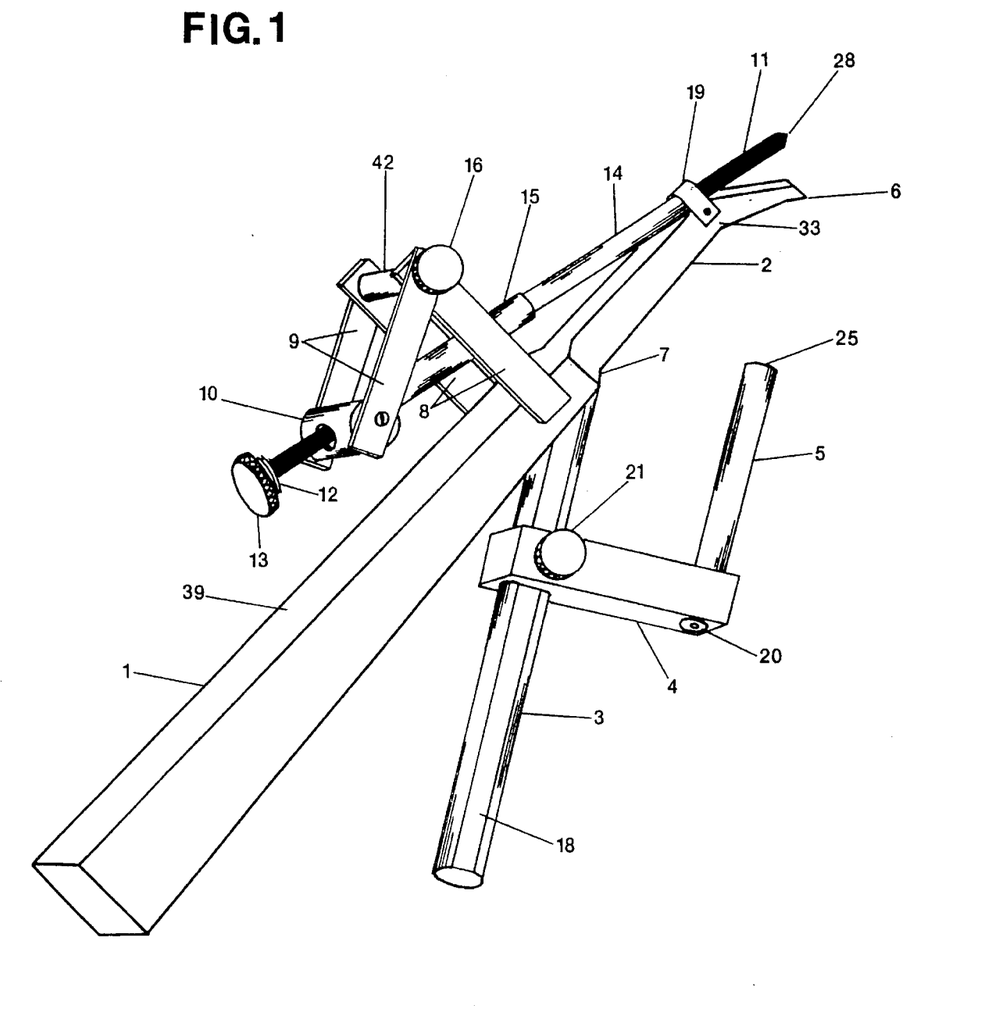
FIG. 1 depicts a three dimensional perspective of the drill guide device with the guide sleeve with conjoined guide sleeve arm positioned on the guide sleeve alignment arm and the secondary reference pointer only partially inserted.

The present invention is configured from the following components as represented in (FIG. 1). A handle (1) which is contiguous with the primary reference pointer (2). The guide sleeve alignment arm (3) that is securely afixed to the body of the handle (1) at a predetermined included angle and is intended to receive the guide sleeve arm (4) which is conjoined with the cannulated guide sleeve (5). The linkage mechanism for variable length adjustment as detailed in (FIG. 2) and the swivel retainer (19) are attached to the handle (1) and to the primary reference pointer (2) respectively, incorporating the coupled external sleeve (15) and internal sleeve (14) for the secondary reference pointer (11). The secondary reference pointer (11) is shown partially inserted in the linkage mechanism for variable length adjustment.

Figure 2:
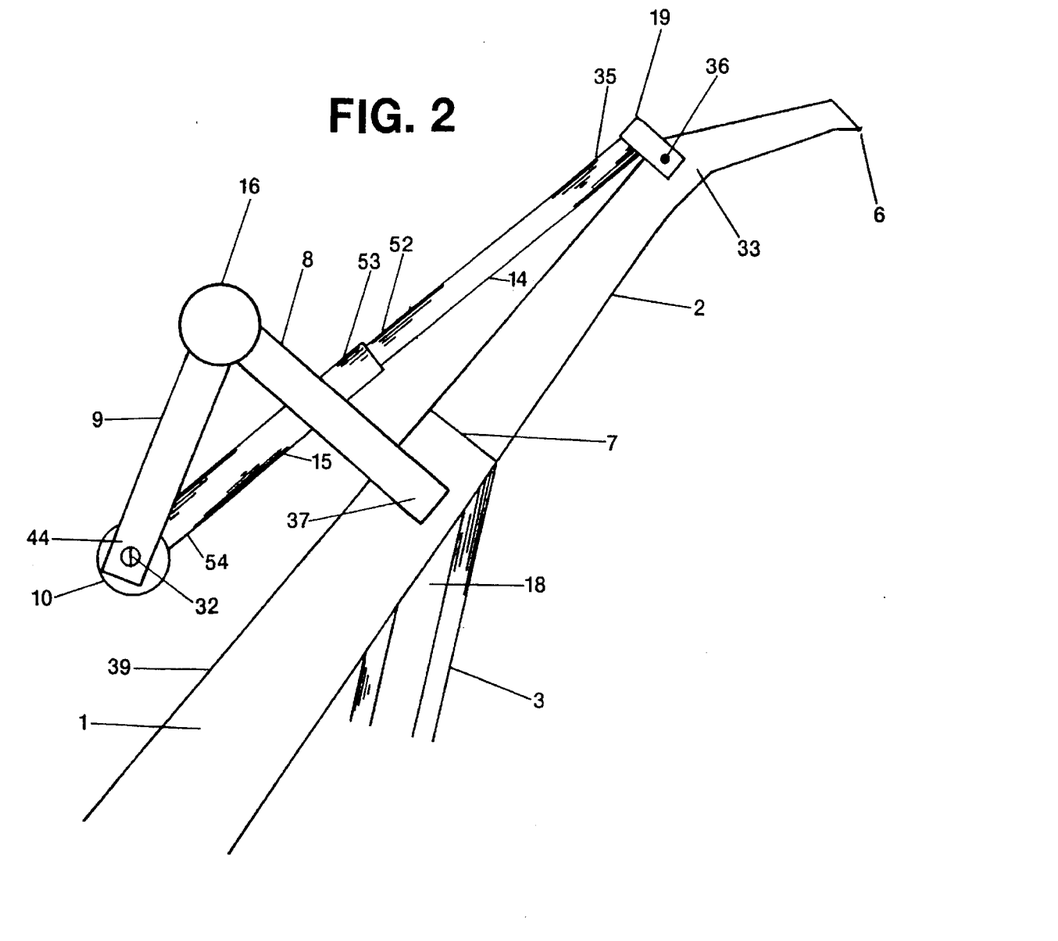
FIG. 2 depicts an enlarged perspective of the linkage mechanism for variable length adjustment with the upright arm, radius arm, barrel, external and internal sleeves for the secondary reference pointer, and the swivel retainer. The above mentioned linkage mechanism is connected to the handle and to the primary reference pointer by means of the upright arms and the swivel retainer, respectively.

As shown in (FIG. 1), the handle (1) is of an elongate structure such that it can be easily and securely grasped by the hand for proper manipulation of the contiguous primary reference pointer (2). It can be in a variety of shapes but for the purpose of simplicity and description, the current embodiment manifests the shape illustrated, having flat sides and somewhat of a rectangular cross-section. The upper surface (39) is shown to be close to a straight plane. The width of the body of the handle (1) should be of such dimension so as to allow sufficient rigidity to the system, in this case it is approximately ten millimeters. It can be seen that the thickness is reduced at the transition area (7) between the body of the handle (1) and the contiguous primary reference pointer (2). The reduced thickness of the primary reference pointer (2) is approximately five millimeters. The shape of the primary reference pointer (2) consists of a straight portion, and a tip (6), as seen in the side profile in (FIG. 2). The included angle represented by the elbow region (33), between the handle (1) and the primary reference pointer (2), is approximately 145 degrees.

The guide sleeve alignment arm (3) is an elongate cylindrical structure with a flat surface (18) incorporated along most of the length, or other such suitable cross sectional shape in order to prevent axial rotation of the slideably engagable guide sleeve arm (4) which is conjoined with the cannulated guide sleeve (5). It is securely affixed to the side opposite of the upper surface (39) of the handle (1) just near the transition area (7), by welding or other suitable means, such that the included angle between the upper surface (39) of the handle (1) and the longitudinal axis of the guide sleeve alignment arm (3) is approximately twenty-eight degrees, as shown in (FIG. 2). The diameter of the guide sleeve alignment arm (3) is on the same order as the width of the handle (1) such that it will provide adequate rigidity to the system.

Figures 4A, 4B:
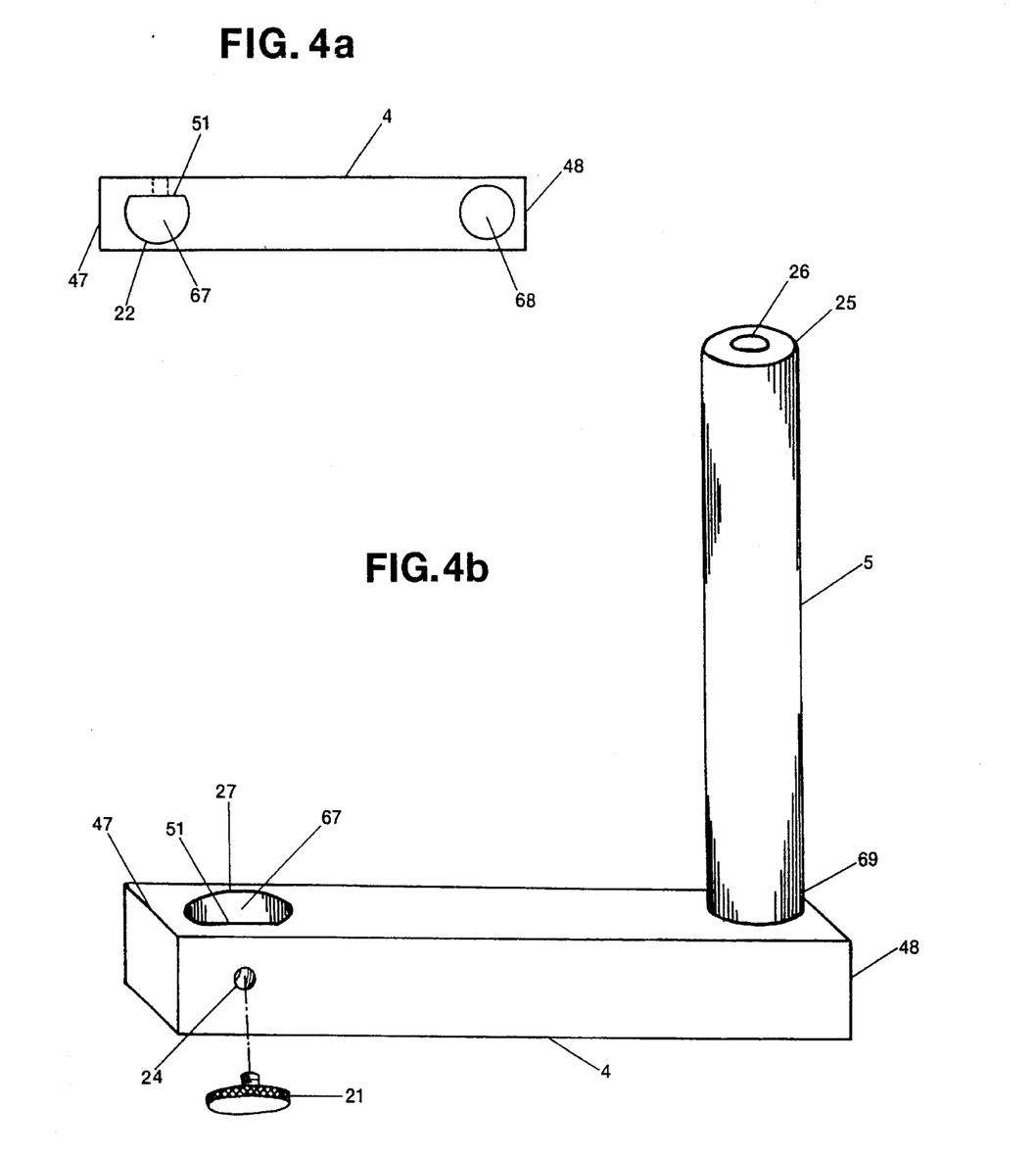
FIG. 4a and 4b depicts the guide sleeve with conjoined guide sleeve arm.

(FIG. 4) demonstrates the guide sleeve (5) with conjoined guide sleeve arm (4). The guide sleeve arm (4) can be rectangular in cross section with a through hole (67) in the first end (47) and a through hole (68) in the second end (48), such that the central axes through the two through holes (67,68) are parallel. The through hole (67) in the first end (47) of the guide sleeve arm (4) has a mating cross section with that of the guide sleeve alignment arm (3). In this application it is represented as a cylindrical cross section with a flat surface (51) incorporated along most of the length, such that the cross sectional shape is other than a round form. A smaller threaded through hole (24) is placed in the first end (47) of the guide sleeve arm (4) such that it intersects the through hole (67) and being substantially perpendicular to the longitudinal axis of the through hole (67). The threads of the smaller threaded through hole (24) will accomodate the threaded portion of the thumb screw (21) in (FIG. 4). The cannulated guide sleeve (5) is an elongated hollow cylindrical structure with a first end (25) and a second end (69). The cannulation in the cannulated guide sleeve (5) maintains a constant diameter along the entire length with a first opening (26) and a second opening (20) located at the first end (25) and the second end (69), respectively, of the cannulated guide sleeve (5). The cannulated guide sleeve (5) has a mating cross section with that of the through hole (68) in the second end (48) of the guide sleeve arm (4) and is conjoined by welding or other suitable means such that they are oriented substantially perpendicular to each other. The internal diameter of the cannulated guide sleeve (5) is such that it will accomodate the standard guide pins (65), in this case the diameter may be between two and four millimeters.

Figure 3:
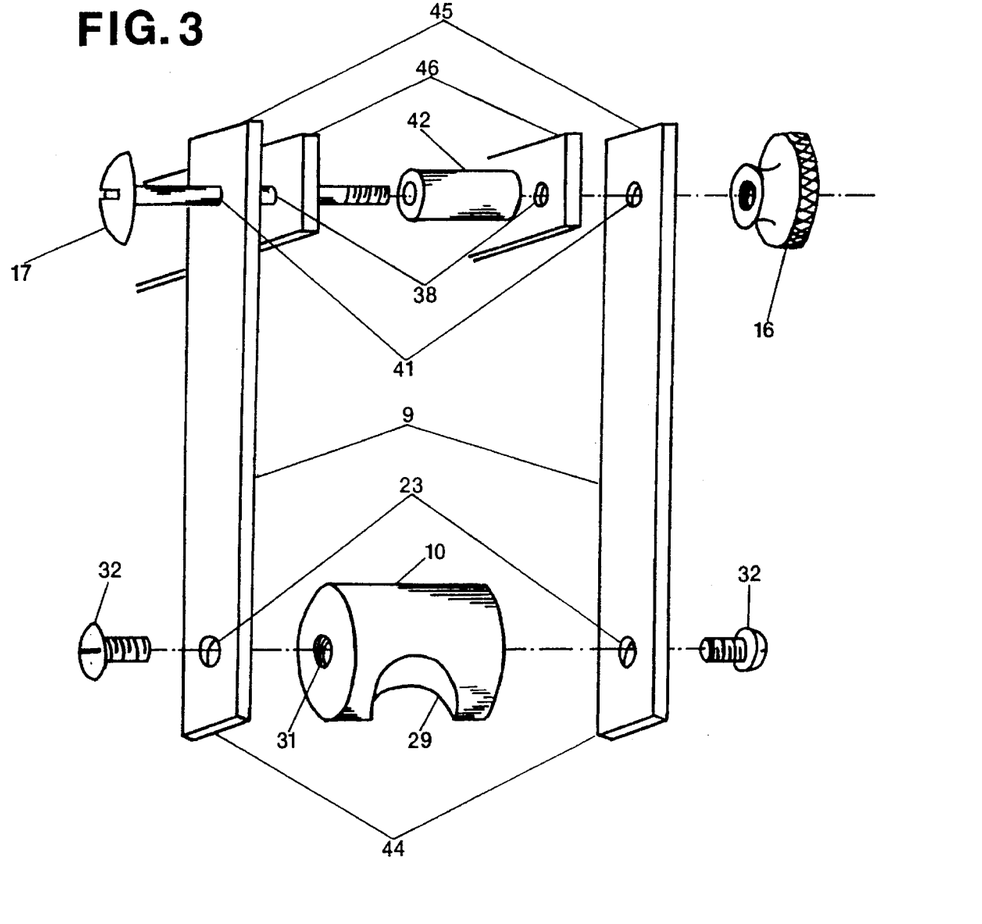
FIG. 3 depicts an exploded perspective of the linkage mechanism for variable length adjustment with detailed arrangement of the components.

(FIG. 2) is an enlarged side profile of the linkage mechanism for variable length adjustment which includes; the upright arms (8), the radius arms (9), the barrel (10), the thumb nut (16), the swivel retainer (19), the external sleeve (15), and the internal sleeve (14) for the secondary reference pointer (11), along with a portion of the handle (1) and the guide sleeve alignment arm (3) and the entire side profile of the primary reference pointer (2). The first ends (37) of the two upright arms (8) are affixed to opposite sides of the body of the handle (1) approximately 50 millimeters from the elbow region (33) by welding or screws or other suitable means. The upright arms (8) are oriented substantially perpendicular to the upper surface (39) of the handle (1) and substantially parallel with each other. A central pivot hole (38), as shown in (FIG. 3), is made in the second end (46) of the upright arm (8), such that when appropriately affixed to the outer sides of the handle (1), the resultant distance between the upper surface (39) of the handle (1) and an axis passing through both central pivot holes (38) is approximately twenty-five millimeters. (FIG. 3) depicts an exploded diagram of a portion of the linkage mechanism for variable length adjustment. Shown in (FIG. 3) one can see the second ends (46) of the upright arms (8) and associated central pivot hole (38) in relationship to the first end (45) of the radius arms (9). A through hole (41) in the first end (45) of the radius arm (9) coincides with the diameter of the central pivot hole (38) in the second end (46) of the upright arm (8). A hollow bushing (42) is positioned between the second ends (46) of the upright arms (8). The threaded bolt for bushing (17) is inserted first into the through hole (41) of the first end (45) of the radius arm (9), then into the central pivot hole (38) of the second end (46) of the upright arm (8), through the hollow bushing (42) into the other central pivot hole (38) of the second end (46) of the upright arm (8), then into and out of the other through hole (41) of the first end (45) of the radius arm (9). The thumb nut (16) is then engaged with the threaded portion of the threaded bolt (17), such that the two parallel radius arms (9) are free to pivot about the central pivot hole (41), unless of course the thumb nut (16) is secured in the tightened position which would then retain the radius arms (9) in a fixed position. Also in (FIG. 3) one can see the relationship of the barrel (10) with the second end (44) of the radius arms (9). Both second ends (44) of the radius arms (9) have a through hole (23), the center of which is located approximately thirty millimeters from the center of the through hole (41) made in the first end (45) of the radius arms (9). The barrel (10) is held in position by two threaded bolts (32) which pass through the through hole (23) in the second end (44) of the radius arm (9) and into the threaded opening (31) in the barrel (10) such that the barrel (10) if free to rotate with respect to the radius arms (9). (FIG. 6) illustrates the details of the design of the barrel (10) which can be formed from a solid cylindrical rod, the length of which is approximately ten millimeters plus twice the thickness of one upright arm (8), and also having a transverse through hole (70) with a first opening (29) and a second opening (30). The external diameter of the barrel (10) being approximately ten to twelve millimeters. The diameter of the transverse through hole (70) corresponds with the external diameter of the second end (54) of the external sleeve (15) for the secondary reference pointer (11) which will be securely affixed in the second opening (30) of the transverse through hole (70) in the barrel (10). A small diameter threaded opening (31) is created in both of the flat ends of the barrel (10) such that the threaded bolt (32) will be accomodated by such threaded opening (31). In addition, the first opening (29) of the transverse through hole (70) in the barrel (10) has a threaded portion (40) such that it will coincide with the threads of the threaded portion (12) of the secondary reference pointer (11). (FIG. 7) shows the details of the swivel retainer (19) and association with the first end (35) of the internal sleeve (14) for the secondary reference pointer (11) and with the elbow region (33) of the primary reference pointer (2). The swivel retainer (19), in this preferred embodiment, is a U shaped strap with a through hole (34) in each of the two limbs, the configuration to the U shaped portion coincides with the external radius of the internal sleeve (14) for the secondary reference pointer (11). Two small diameter pins (36) can be utilized to swivelly couple the limb portions of the swivel retainer (19) to the elbow region (33) of the primary reference pointer (2) such that the combined internal sleeve (14) for the secondary reference pointer (11) and the swivel retainer (19) are free to swivel about the two small diameter pins (36). In order to complete the coupling of the linkage mechanism for variable length adjustment with the combined internal sleeve (14) for the secondary reference pointer (11) and swivel retainer (19), it is necessary that the second end (52) of the internal sleeve (14) for the secondary reference pointer (11) be inserted into the opening of the first end (53) of the external sleeve (15) for the secondary reference pointer (11) such that the external sleeve (15) is free to slide over the internal sleeve (14), much like the action of a telescope. It is obvious that the external diameter of the internal sleeve (14) for the secondary reference pointer (11) coincides with the internal diameter of the external sleeve (15) for the secondary reference pointer (11). Both the internal sleeve (14) and the external sleeve (15) for the secondary reference pointer (11) are hollow tubular structures which maintain substantially consistent outside and inside diameter dimensions along their respective lengths.

Figure 5:
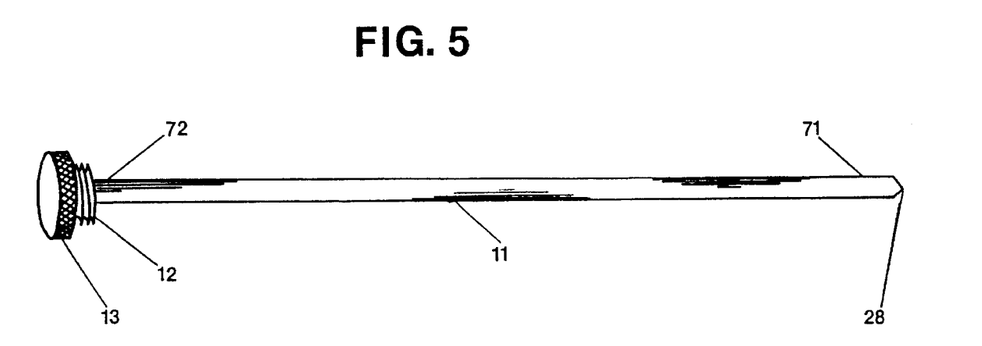
FIG. 5 depicts the secondary reference pointer.
Figure 6A:
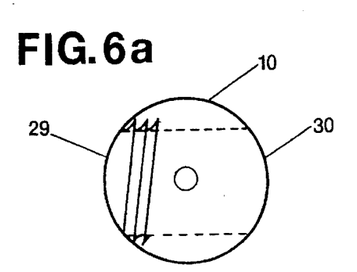
FIG. 6a, FIG. 6b, FIG. 6c and FIG. 6d depicts the barrel component of the linkage mechanism for variable length adjustment.
Figure 6B:
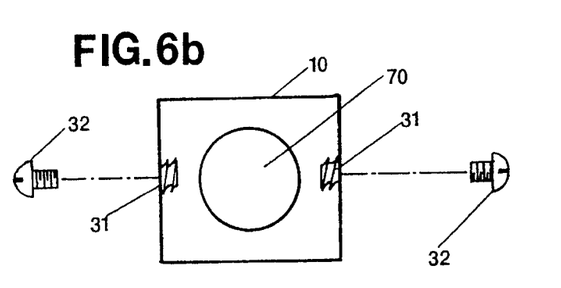
Figure 6C:
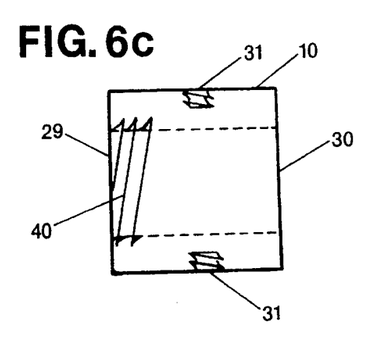
Figure 6D:
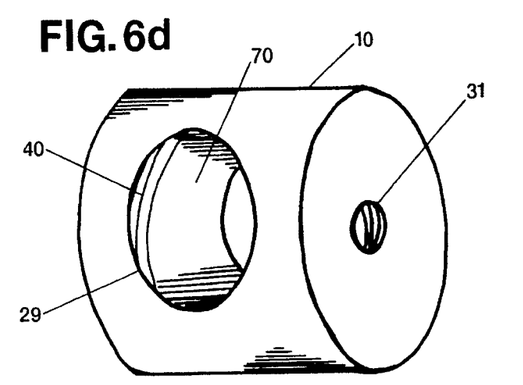
Figures 7A, 7B:
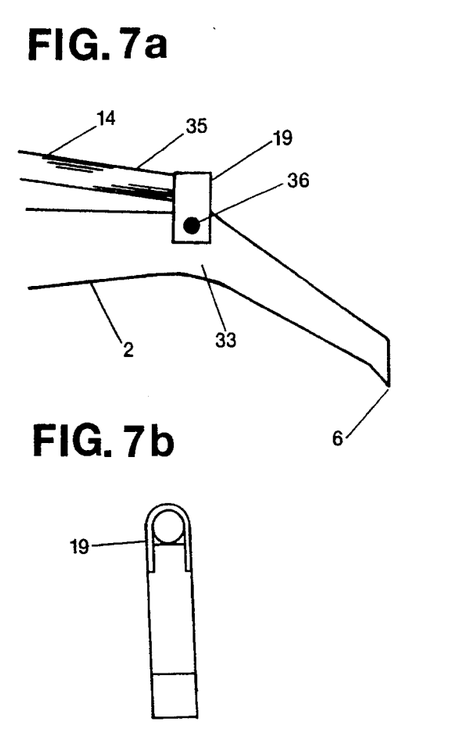
FIG. 7a, FIG. 7b and FIG. 7c depicts the swivel retainer mechanism which swivelly retains the end of the internal sleeve for the secondary reference pointer to the elbow region of the primary reference pointer.
Figure 7C:
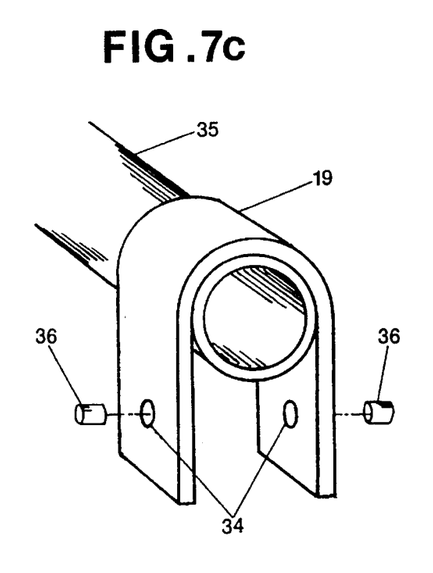

The secondary reference pointer (11), as shown in (FIG. 5), is configured from a small diameter solid cylindrical rod with a first end (71) and a second end (72). The first end (71) forms a conical shape, also known as the tip (28). The second end (72) is connected to the larger diameter threaded portion (12). The threaded portion (12) is of such a configuration that it will be accomodated by the threaded portion (40) of the first opening (29) of the through hole (70) in the barrel (10). Immediately adjacent and intimately attached to the threaded portion (12) is the knurled end (13) which is convenient for grasping and manipulation of the secondary reference pointer (11).

The mechanics of the present invention are best represented in (FIG. 1), particularly in terms of the linkage mechanism for variable length adjustment. It can be seen that the combined radius arms (9) and barrel (10) are free to travel in a predetermined arcuate motion about the central pivot hole (38) in the second ends (46) of the upright arms (8). The contour of this predetermined arcuate motion corresponds to approximately 30 millimeter radius about the central pivot hole (38) and is important in order for the tip (28) on the first end (71) of the secondary reference pointer (11), once it has been properly inserted and engaged with the threaded portion (40) in the first opening (29) of the through hole (70) in the barrel (10), to follow a straight path coinciding with the centerline which passes along the longitudinal axis of the engaged cannulated guide sleeve (5) and intersects the point represented by the tip (6) of the primary reference pointer (2). It is therefore critical to the scope of this invention, following any adjustment of the linkage mechanism for variable length adjustment, that the tip (28) of the secondary reference pointer (11) will travel in a straight line, and that this straight line coincides with the centerline which passes through the longitudinal axis of the cannulated guide sleeve (5) and intersects the point represented by the tip (6) of the primary reference pointer (2). In other words, the centerline represents the path that the guide pin (65) will follow during the drilling procedure.

Figure 8:
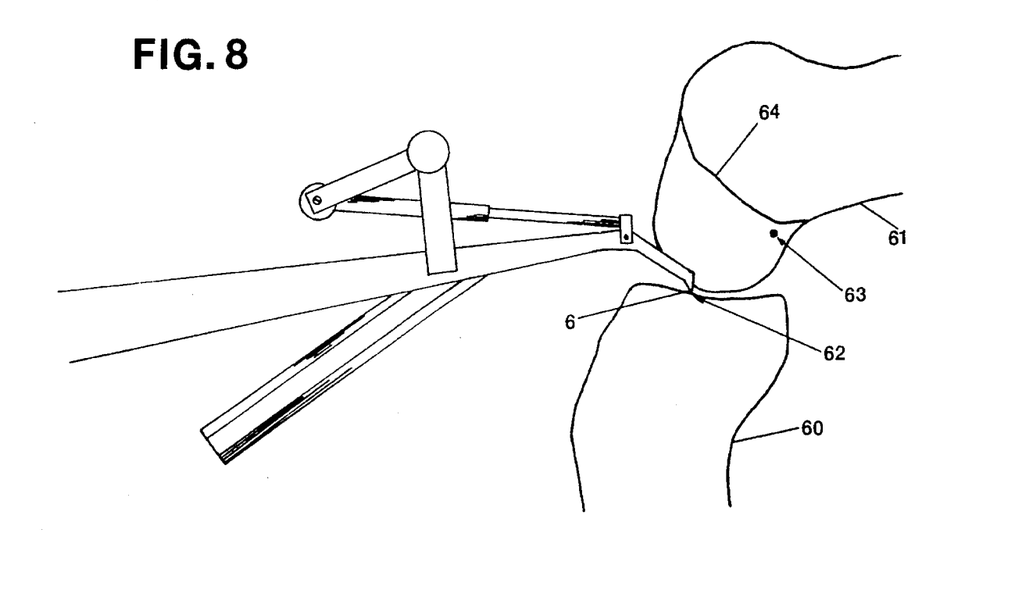
FIG. 8 depicts the tip of the primary reference pointer properly positioned on the insertion site of the ACL on the tibial plateau. (This is a medial view of a right knee positioned in approximately ninety degrees of flexion with a sagittal cut through the femur).

This may be better demonstrated by diagrams illustrating the use of this drill guide device in a knee model as represented in the following figures. For the purpose of description of detail, the knee model will be represented by a medial view of the right knee positioned in approximately ninety degrees of flexion. The schematic drawing of the knee, as seen in (FIG. 8), depicts the proximal tibia (60) and the insertion site (62) for the ACL on the tibial plateau. The distal femur (61) is represented by sagittal section, thereby revealing the site of the anatomic origin of the ACL on the medial surface of the lateral femoral condyle and the relationship to Blumenstad's line (64).

Figure 9:
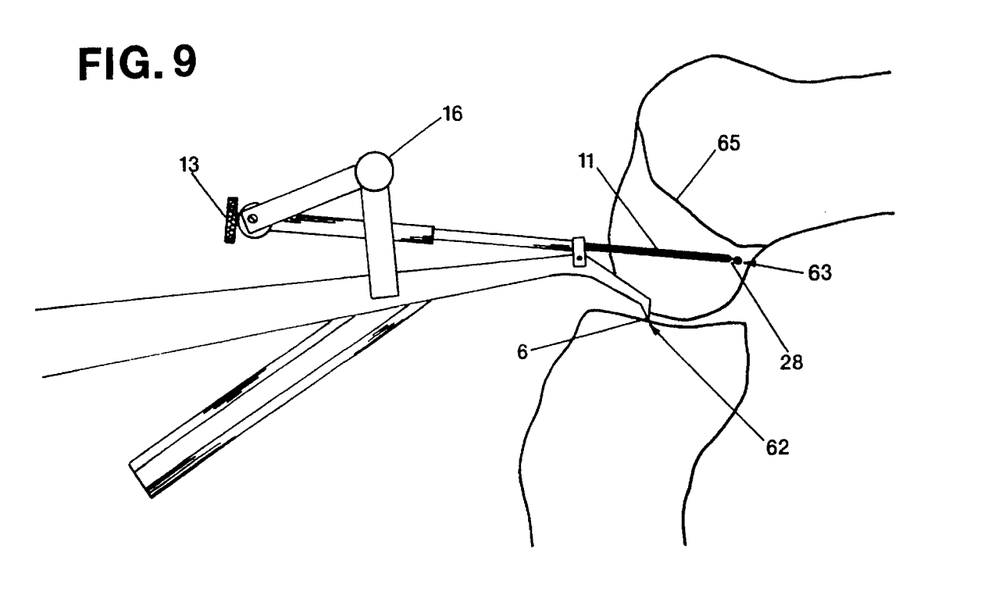
FIG. 9 depicts the secondary reference pointer completely inserted, with the tip located on the anatomic site of the origin of the ACL.
Figure 10:
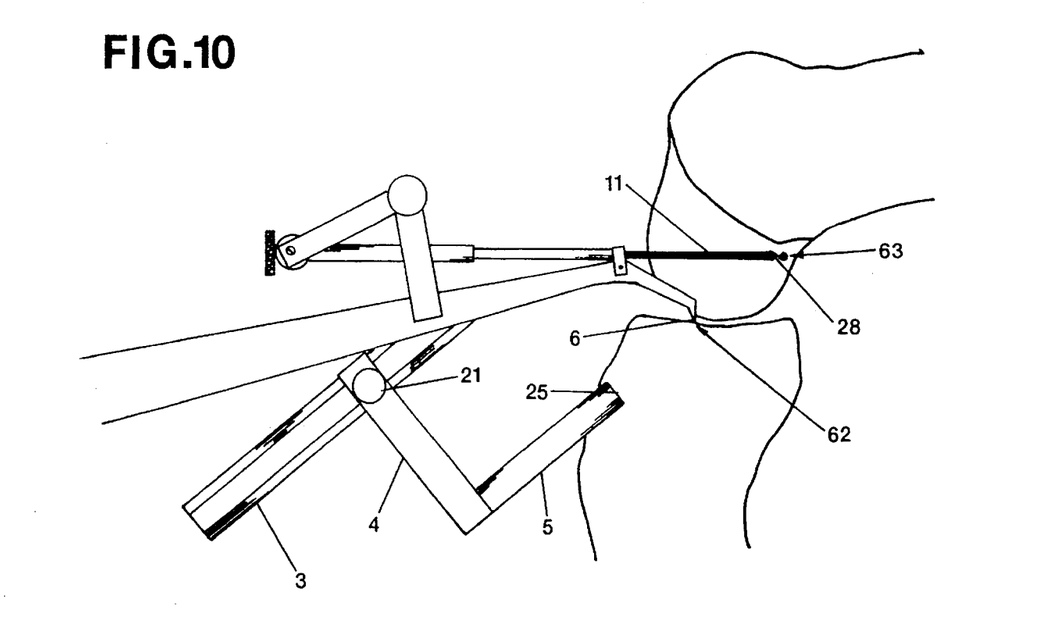
FIG. 10 depicts the guide sleeve with conjoined guide arm properly positioned on the guide sleeve alignment arm and secured against the tibial cortex.
Figure 11:
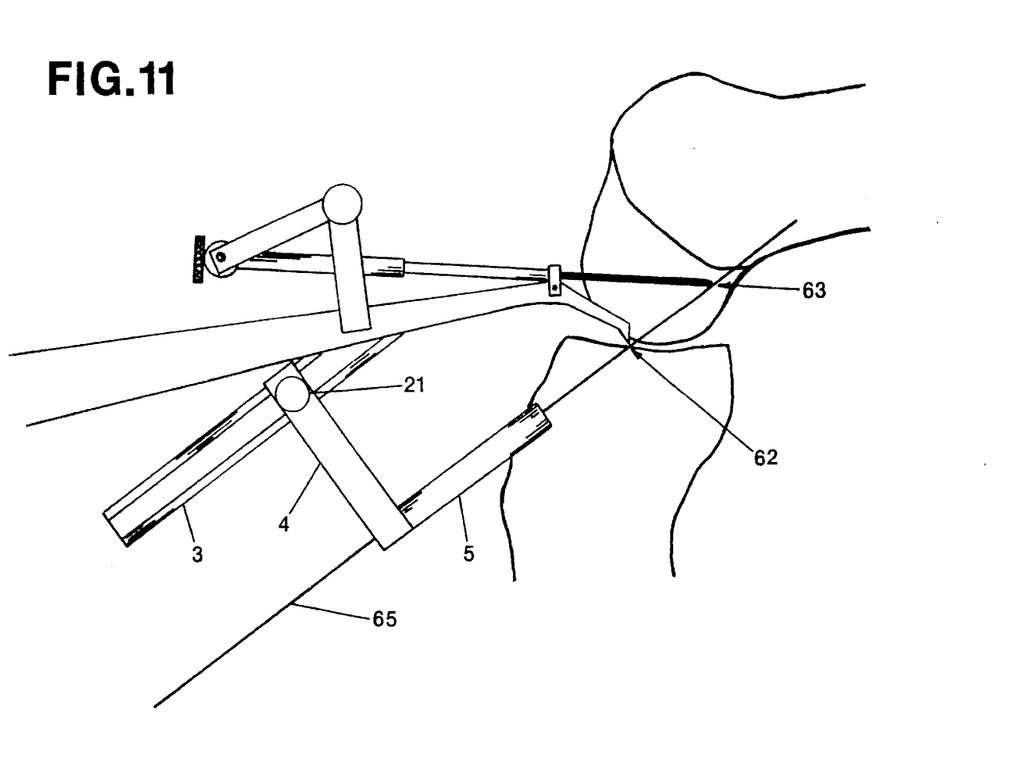
FIG. 11 depicts the placement of a guide pin through the cannulated guide sleeve, across the tibial metaphysis, intersecting both attachment sites of the ACL and into the femur.

(FIG. 8) shows the device without the secondary reference pointer (11) or the guide sleeve (5) with conjoined guide sleeve arm (4) engaged. The tip (6) of the primary reference pointer (2) is passed through the antero-medial portal and located on the insertion site (62) of the ACL while under arthroscopic visualization. While the device is held in this position the secondary reference pointer (11) is made ready for insertion and engagement. (FIG. 9) illustrates the secondary reference pointer (11) completely inserted and properly engaged. The linkage mechanism for variable length adjustment is manipulated while arthroscopically visualizing the placement of the tip (28) of the secondary reference pointer (11) on the site of the anatomic origin (63) of the ACL. Once the tip (28) is accurately located, the thumb nut (16) is tightened in order to temporarily secure the linkage mechanism for variable length adjustment in that position. While the device is maintained in the predetermined position, the guide sleeve (5) with conjoined guide sleeve arm (4) is slideably engaged with the guide sleeve alignment arm (3), such that the free end of the guide sleeve alignment arm (3) is introduced into the first opening (27) of the through hole (67) at the first end (47) of the guide sleeve arm (4) and slideably advanced until the first end (25) of the cannulated guide sleeve (5) comes in contact with the external tibial cortex, as shown in (FIG. 10). With the drill guide device maintained in this position, the thumb screw (21) is tightened in order to temporarily secure the guide sleeve (5) with conjoined guide sleeve arm (4), thereby providing for the system to be self retaining. (FIG. 11) demonstrates the resultant position of the guide pin (65) once it has been drilled into position. At this point the drill guide device is removed by first loosening the thumb screw (21) and slideably withdrawing the guide sleeve (5) with conjoined guide sleeve arm (4) from both the guide sleeve alignment arm (3) and the preplaced guide pin (65). Subsequently the knurled end (13) of the secondary reference pointer (11) is grasped and rotated in order to disengage the threaded portion (12) of the secondary reference pointer (11) from the threaded portion (40) of the first opening (29) of the through hole (70) of the barrel (10). After the secondary reference pointer (11) is retracted, the primary reference pointer (2) is extracted from the antero-medial portal. All that remains now is to drill the bone tunnels utilizing an appropriate diameter cannulated drill bit by allowing it to follow the preplaced guide pin (65).

There are several aspects of the present invention which demonstrate it to be novel above and beyond previously disclosed drill guide concepts. The first and foremost is the ability of the current embodiment to allow for a means to locate and to simultaneously select, by means of reference pointers, both the anatomic origin and insertion sites of the ACL. By virtue of this method a straight tibio-femoral bone tunnel which precisely intersects the anatomic origin and insertion sites of the ACL can accurately and repeatably be created while the knee is maintained in approximately ninety degrees of flexion.

A second novel feature of the present invention is that the linkage mechanism for variable length adjustment, inherent in the principle concept the drill guide device of the current embodiment, allows one drill guide device to be utilized on different size patients, thereby obviating the need for various configurations of drill guides to accomodate the various ACL length discrepancies among different patients. The linkage mechanism for variable length adjustment provides a method by which the tip of the primary reference pointer and the tip of the secondary reference pointer will always remain on the centerline through the longitudinal axis of the guide sleeve regardless of variation in length between the ACL attachment sites.

A third novel feature of the present invention is that the design of the drill guide device is such that the entire preparation of the tibial and femoral bone tunnel is performed through the tibial skin incision and through an arthroscopic portal. A femoral cut down procedure is not necessary, as is with many other types of drill guide devices.

A further novel feature of the drill guide device of the present invention is that as a result of the alignment of the straight tibio-femoral bone tunnel, the axis through the center of the tibial tunnel and the axis through the center of the intra-articular segment will remain in a near straight line throughout the full range of motion. This is an important factor in that adverse stress concentrations that would normally be imposed on the graft segment as it enters the tibial tunnel on the tibial plateau will be greatly minimized.

Although the drill guide device described herein is useful for directing bone tunnel placement for reconstruction of the ACL, it is not restricted only to ACL applications but that the principle concepts embodied in the present invention would allow it to be used in other applications as well.

It is the preferred embodiment of the present invention, as described in the scope to this application, that discloses an ACL drill guide device for directing a straight bone tunnel in the tibia and femur precisely intersecting the attachment sites of the ACL. This preferred embodiment is for purposes of example only and that subsequent modifications or variations to the device are possible and are to be expected, although they will encompass the fundamental embodiments of the scope of the claims.

I claim:

1. An orthopedic drill guide device providing for the simultaneous selection of two reference points thereby allowing for the sequential drilling of two separate bone tunnels in a straight line incorporating both reference points comprising:

(a) a handle;

(b) a guide sleeve;

(c) a linkage mechanism for variable length adjustment;

said handle being an elongate member having a first end and a second end whereby said first end is utilized to direct and manipulate the device, said second end being substantially contiguous with said first end and oriented at a first predetermined angle relative to that of said first end, a terminal end of said second end tapers to a point forming a tip of a primary reference pointer thereby providing facilitating means for the positioning of said tip at a predetermined reference point, an alignment arm having a longitudinal axis and being attached at a second predetermined angle relative to an upper surface of said handle;

said guide sleeve being an elongated tube with a longitudinal axis having a first and second end, said elongated tube second end is conjoined with a guide arm by attachment means, said guide arm being an elongated member having a first end with a through hole and a second end with a through hole such that the longitudinal axes through both said through holes are oriented substantially parallel, said second end of said guide sleeve is rigidly affixed in said through hole of said second end of said guide arm such that the longitudinal axis of said guide arm is oriented substantially perpendicular to the longitudinal axis of said guide sleeve, said through hole of said first end of said guide arm having a substantially similar mating cross section with that of said alignment arm whereby when said through hole of said first end of said guide arm slideably receives said alignment arm a centerline corresponding with an extension of the longitudinal axis of said guide sleeve will intersect said tip of said primary reference pointer;

said linkage mechanism for variable length adjustment is attached to said handle and includes a plurality of components coupled together and includes means for providing a predetermined arcuate motion to be translated into a resultant linear motion to a tip of a secondary reference pointer such that said tip of said secondary reference pointer will travel in a linear path coinciding with a centerline which is a direct extension of the longitudinal axis of said guide sleeve intersecting the point represented by the tip of said primary reference pointer of said second end of said handle and the tip of said secondary reference pointer.

2. The drill guide device of claim 1 wherein the first predetermined angle is approximately 145 degrees.

3. The drill guide device of claim 1 wherein said second predetermined angle between the upper surface of said first end of said handle and the longitudinal axis of said alignment arm is approximately 28 degrees.

4. The drill guide device of claim 1 wherein said linkage mechanism for variable length adjustment comprises two opposing substantially parallel upright arms having first and second ends such that said first ends of said upright arms are attached by securing means to opposite sides of said handle, said upright arms being oriented substantially perpendicular relative to said upper surface of said handle and being positioned along the longitudinal axis of said handle approximately 50 millimeters from said junction of said first and second ends of said handle, a central pivot hole in said second end of each of said upright arms is oriented approximately 25 millimeters from said upper surface of said handle, and a swivel retainer swivelly attached at said junction of said first and second ends of said handle.

5. The drill guide device of claim 4 wherein said linkage mechanism for variable length adjustment further comprises two opposing substantially parallel radius arms having first and second ends with through holes in said first and second ends such that the distance between said through holes is approximately 30 millimeters, said through holes in said first ends of said radius arms are pivotally coupled by hinged means to said central pivot holes in said second ends of said upright arms, a barrel comprising a segment of cylindrical rod with a through hole along the longitudinal axis of the cylindrical rod is intercalated by axial rotational means between said through holes in said second ends of said radius arms such that manipulated movement of said second ends of said radius arms about said hinged means results in an arcuate motion corresponding with a radius of approximately 30 millimeters.

6. The drill guide device of claim 5 wherein an external and internal sleeve, each with a first and second end, form a telescopic channel means for said secondary reference pointer, said telescopic channel links said barrel with said swivel retainer such that the swivel retainer provides a fulcrum means to pivotally hinge said first end of said internal sleeve to said junction of said handle.

7. The drill guide device of claim 6 wherein said secondary reference pointer is retractable for a predetermined distance into the telescopic channel means of said external and internal sleeves thereby providing a means by which said primary reference pointer in association with the retracted secondary reference pointer can be inserted through a small opening.

8. The drill guide device of claim 7 wherein said reference point selected by said tip of said primary reference pointer is adapted to be the approximate insertion site of an anterior cruciate ligament on a tibial plateau.

9. The drill guide device of claim 7 further comprising engaging means for engaging a second end of said secondary reference pointer and said barrel, said engaging means including a male threaded portion of said second end of said secondary reference pointer and a female threaded portion of a first opening of said barrel.

10. The drill guide device of claim 9 wherein the barrel is secured in a predetermined position by a thumb nut means whereby said tip of said secondary reference pointer may be positioned on a reference point coinciding with the centerline of the guide sleeve.

11. The drill guide device of claim 10 wherein said reference point is adapted to be the approximate site of origin of the anterior cruciate ligament in a femoral intercondylar notch.

12. The drill guide device of claim 5 wherein the hinged means used to pivotally couple said radius arms with said upright arms comprises a threaded bolt passing through said central pivot holes and through a hollow bushing and engaged with a thumb nut such that said hinged means will allow for securing said radius arms in a predetermined position relative to said upright arms.

* * * * *